(12) United States Patent
Whitman et al.

(10) Patent No.: US 9,176,103 B2
(45) Date of Patent: Nov. 3, 2015

(54) CHEMICAL INDICATOR COMPOSITIONS, INDICATORS AND METHODS

(75) Inventors: David A. Whitman, St. Paul, MN (US); David M. Read, White Bear Lake, MN (US); Ranjani V. Parthasarathy, Woodbury, MN (US); Kevin D. Landgrebe, Woodbury, MN (US); Anthony E. Bennett, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 637 days.

(21) Appl. No.: 13/161,079

(22) Filed: Jun. 15, 2011

(65) Prior Publication Data

US 2011/0312096 A1  Dec. 22, 2011

Related U.S. Application Data

(60) Provisional application No. 61/357,059, filed on Jun. 21, 2010.

(51) Int. Cl.
G01N 21/78 (2006.01)
G01N 31/22 (2006.01)

(52) U.S. Cl.
CPC .............. *G01N 31/226* (2013.01); *G01N 21/78* (2013.01)

(58) Field of Classification Search
CPC ..................................................... G01N 21/78
USPC ............ 106/31.13, 31.16; 116/206–207, 216; 252/408.1; 374/161–162; 422/11, 26, 422/402, 420, 425, 430; 436/1–2, 164, 166, 436/169
See application file for complete search history.

(56) References Cited

U.S. PATENT DOCUMENTS

| | | | |
|---|---|---|---|
| 1,844,199 A * | 2/1932 | Bicknell et al. | 346/134 |
| 2,118,144 A | 8/1932 | Berman et al. | |
| 1,924,793 A * | 8/1933 | Laske | 106/287.18 |
| 2,625,494 A * | 1/1953 | Morrison | 503/202 |
| 2,889,799 A * | 6/1959 | Korpman | 116/207 |
| 3,313,266 A * | 4/1967 | Kelson | 116/207 |
| 3,360,338 A | 12/1967 | Edenbaum | |
| 3,360,339 A | 12/1967 | Edenbaum | |
| 3,386,807 A | 6/1968 | Edenbaum | |
| 3,471,422 A | 10/1969 | Edlein et al. | |
| 3,616,898 A * | 11/1971 | Massie | 206/216 |
| 4,121,011 A * | 10/1978 | Glover et al. | 428/347 |
| 4,424,990 A * | 1/1984 | White et al. | 285/381.2 |
| 4,514,361 A | 4/1985 | Hirsch | |
| 4,579,715 A | 4/1986 | Bruso | |
| 5,057,433 A | 10/1991 | Douglas | |
| 5,064,576 A | 11/1991 | Suto | |
| 5,855,655 A * | 1/1999 | Nohr et al. | 106/31.27 |
| 5,916,816 A | 6/1999 | Read | |
| 6,168,655 B1 * | 1/2001 | Nohr et al. | 106/31.58 |
| 6,485,978 B1 * | 11/2002 | Kirckof et al. | 436/1 |
| 6,488,890 B1 * | 12/2002 | Kirckof | 422/403 |
| 6,884,394 B1 * | 4/2005 | Hehenberger et al. | 422/404 |
| 7,718,433 B2 * | 5/2010 | Stecklein et al. | 436/10 |
| 2011/0275159 A1 | 11/2011 | Landgrebe | |

FOREIGN PATENT DOCUMENTS

| | | |
|---|---|---|
| GB | 1132334 | 10/1968 |
| JP | 02211162 | 8/1990 |
| JP | 04364174 | 12/1992 |
| JP | 10-513502 | 12/1998 |
| JP | 2002322315 | 11/2002 |
| JP | 2002323451 | 11/2002 |
| JP | 2004-317433 | * 11/2004 |
| JP | 2005-329983 | * 12/2005 |
| JP | 2006-1206 | * 1/2006 |
| JP | 2006-3274 | * 1/2006 |
| JP | 2006104346 | 4/2006 |
| JP | 2008-517911 | 5/2008 |
| WO | WO 97/20000 | 6/1997 |
| WO | WO 98/13431 | 4/1998 |
| WO | WO 2006/047080 | 5/2006 |
| WO | WO 2010/078422 | 7/2010 |

OTHER PUBLICATIONS

Derwent Abstract for JP 02-211162 1990, 1 page.*
Mamylov, S. et al, Journal of Thermal Analysis 1988, 33, 543-546.*
Ferris, S. W. et al, Industrial & Engineering Chemistry Analytical Edition 1934, 6, 23-29.*
Touchstone, J. C. et al, Analytical Chemistry 1971, 43, 858-863.*
MacDonald, G. A. et al, Journal of Agriculture and Food Chemistry 1996, 44, 106-112.*

* cited by examiner

*Primary Examiner* — Arlen Soderquist

(57) ABSTRACT

Chemical indicator compositions comprising a bismuth compound; elemental sulfur; and a compound with relatively high water solubility which makes the composition alkaline when exposed to water vapor at an elevated temperature; a chemical indicator comprising a substrate and the composition coated on at least a portion of a major surface of the substrate; and methods of making and using the chemical indicator are disclosed.

19 Claims, 1 Drawing Sheet

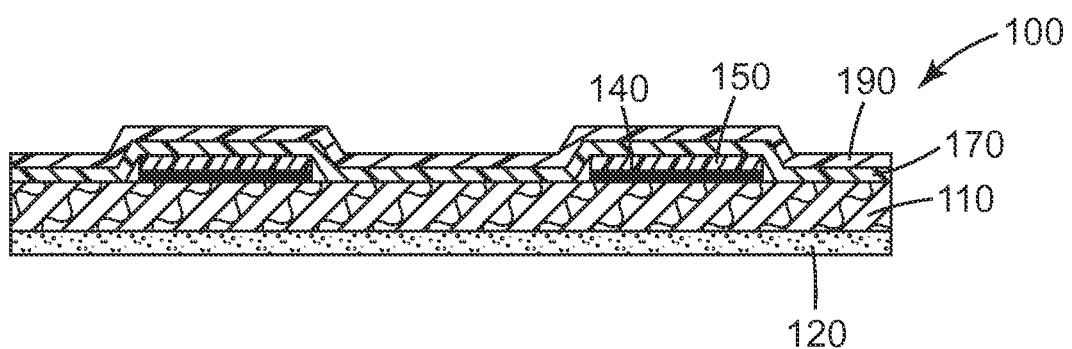

CHEMICAL INDICATOR COMPOSITIONS, INDICATORS AND METHODS

CROSS-REFERENCE TO RELATED APPLICATION

This application claims priority to U.S. Provisional Patent Application No. 61/357,059, filed Jun. 21, 2010, the disclosure of which is incorporated by reference herein in its entirety."

BACKGROUND

A variety of products and articles, including, for example, medical instruments, devices, and equipment, must be sterilized prior to use to prevent bio-contamination of a wound site, a sample, an organism, or the like. A number of sterilization processes are used that involve contacting the product or article with a sterilant. Examples of such sterilants include steam, ethylene oxide, hydrogen peroxide, and the like. Steam sterilization is widely used, at least in part because multiple batches of articles can be subjected to sterilization conditions during a 24 hour period using a single steam sterilizer.

Monitoring for conditions sufficient for sterilization is generally carried out by placing an appropriate sterilization indicator along with the product and/or article to be sterilized within a sterilization chamber. A variety of sterilization indicators, including chemical and biological indicators, are known and used for this purpose. Chemical indicators offer an advantage in that they can be read immediately at the end of a sterilization process. Internal chemical indicators are placed within an instrument tray and are read in the operating room upon opening the steam-exposed tray prior to instrument removal. Process indicators, such as labels and autoclave tapes, indicate that a wrapped instrument tray or other wrapped article or articles has been exposed to steam.

Internal chemical indicators and process indicators, such as autoclave tapes, should indicate (by color change) the presence of steam under various operating conditions but should remain their original color, or near their original color, under other conditions in which inadequate amounts of steam for sterilization of medical devices has contacted them. For example, an autoclave tape should show a significant color change when subjected to steam in a hospital autoclave at 132-134° C. for around 3 or 4 minutes and at 121° C. for around 20 minutes. Additionally, when tested using a steam resistometer, and according to ISO Standard 11140, an autoclave tape should show a significant color change on contact with steam at 134° C. for 2 minutes, and at 121° C. for 10 minutes, but should not show a significant color change on exposure to steam at 134° C. for 30 seconds nor at 121° C. for 3 minutes. Finally, an autoclave tape should not show a significant color change on exposure to dry heat at 140° C. for 30 minutes.

Steam sterilization indicator compositions for both internal indicators and process indicators that have been used include a polyvalent metal compound, such as lead carbonate, and sulfur. Such indicators turn to brown or black when their color is fully developed by a steam sterilization condition. Because of environmental concerns, lead compounds have been and continue to be replaced by other polyvalent metal compounds. For example, bismuth has been proposed to replace lead in certain steam sterilization indicator compositions as described in U.S. Pat. No. 5,916,816 (Read) wherein, for example, bismuth subcarbonate was used.

Accordingly, there is a continuing need for lead-free chemical indicators that can indicate that a steam sterilization process condition has been met.

SUMMARY

The present disclosure provides a chemical indicator composition, a chemical indicator including the composition, an autoclave tape including the composition, and a method of determining the effectiveness of a sterilization process using the chemical indicator composition.

In one embodiment, there is provided a chemical indicator composition comprising:
   a) a bismuth (III) compound selected from the group consisting of bismuth (III) oxide and a bismuth (III) compound comprising at least one organic group which includes 2 to 20 carbon atoms;
   b) elemental sulfur; and
   c) a compound with relatively high water solubility that makes the composition alkaline when exposed to water vapor at an elevated temperature;
   wherein when the composition is coated on a substrate comprising a saturant and exposed to a first condition of steam at a temperature of 134° C. for 2 minutes, the composition undergoes a change in optical density resulting in an optical density of at least 0.8, and wherein when instead exposed to a second condition of steam at a temperature of 121° C. for 3 minutes, any change in optical density is at least 0.1 optical density units less than when exposed to the first condition.

In another embodiment, there is provided a chemical indicator composition comprising:
   a) a bismuth (III) compound selected from the group consisting of bismuth (III) oxide and a bismuth (III) compound comprising at least one organic group which includes 2 to 20 carbon atoms;
   b) elemental sulfur; and
   c) a compound with relatively high water solubility, selected from the group consisting of potassium carbonate, potassium bicarbonate, and sodium phosphate, which makes the composition alkaline when exposed to water vapor at an elevated temperature.

In another embodiment, there is provided a chemical indicator composition comprising:
   a) a bismuth compound;
   b) a sulfur compound or elemental sulfur; and
   c) a reducing agent; and
   d) a compound which makes the composition alkaline when exposed to water vapor at an elevated temperature.

A chemical indicator and/or a tape is also provided, comprising a substrate and any of the above chemical indicator compositions coated on at least a portion of a major surface of the substrate. Any one of the above compositions includes any one embodiments thereof described herein.

In another embodiment, there is provided a method of determining the effectiveness of a steam sterilization process, the method comprising:
   providing any one of the above chemical indicators and/or tapes comprising the chemical indicators compositions described herein;
   placing the chemical indicator and/or tape in a steam sterilization chamber;
   exposing the chemical indicator and/or tape to steam at a temperature of at least 121° C.; and determining an optical density of the chemical indicator and/or tape.

Definitions

The term "black" as used herein refers to the color black as is commonly known and distinguished from other colors (i.e., not green or brown or yellow, etc.).

The term "Class 1 indicator" or "Class 1 chemical indicator" refers to a chemical indicator for steam, which when tested using a resistometer undergoes a visible change as specified by ISO/FDIS11140-1(2005).

The term "Class 4 indicator" or "Class 4 chemical indicator" as used herein is identical to that specified by ISO/FDIS11140-1 (2005), that is, it refers to a chemical indicator for steam, which when tested using a resistometer undergoes a visible change as specified by the manufacturer on exposure to steam at its stated value (for example, 134° C. for 3.5 minutes) and does not undergo a visible change or undergoes a change that is markedly different as specified by the manufacturer on exposure to steam at the stated value minus 25 percent of the stated value time and minus 2 degrees from the stated value temperature.

The term "comprising" and variations thereof (e.g., comprises, includes, etc.) do not have a limiting meaning where these terms appear in the description and claims.

The term "relatively high water solubility" as used herein refers to a compound that has solubility in water at around 20° C. of at least 5 grams/100 ml or greater.

The term "reducing agent" means a compound capable of donating an electron or a hydrogen. In particular, the reducing agents described herein are capable of reducing a sulfur-sulfur bond, and more particularly, capable of reducing elemental sulfur to a thiol compound.

The term "thiol" as used herein refers to a compound containing a functional group composed of a sulfur-hydrogen bond.

As used herein, "a," "an," "the," "at least one," and "one or more" are used interchangeably, unless the context clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Also herein, the recitations of numerical ranges by endpoints include all numbers subsumed within that range (e.g., a weight ratio of not more than 2:3 and not less than 0.5:3 includes a weight ratio of 2:3, 1.9:3, 1.75:3, 1:3, 0.61:3, 0.5:3, etc.).

The above summary of the present invention is not intended to describe each disclosed embodiment or every implementation of the present invention. The description that follows more particularly exemplifies illustrative embodiments.

BRIEF DESCRIPTIONS OF THE DRAWINGS

FIG. 1 is a cross-sectional view of an exemplary chemical indicator described herein in a tape form.

DETAILED DESCRIPTION OF ILLUSTRATIVE EMBODIMENTS OF THE INVENTION

Chemical indicator compositions have been found that comprise certain bismuth compounds and compounds that are relatively highly soluble in water and make the indicator compositions alkaline when exposed to water vapor at an elevated temperature, and/or at least one reducing agent. Surprisingly, the chemical indicator compositions are useful in chemical indicators such as internal chemical indicators and process indicators, including especially autoclave tapes. This finding is surprising because previously it had been generally considered that relatively highly water soluble base compounds in chemical indicator compositions, and indicators using the compositions, had color changes that were too dark upon exposure to levels of steam inadequate to effect sterilization.

It has also been found, surprisingly, that reducing agents can be can be used in combination with compounds with relatively high water solubility to produce chemical indicator compositions and chemical indicators that enhance darkening on exposure to steam.

It has also been found that dyes and pigments, when added to the above compositions, can effect a color change to black on exposure to steam when the composition devoid of pigment would only turn brown on exposure to steam.

In one embodiment, there is provided a chemical indicator composition comprising: a bismuth (III) compound selected from the group consisting of bismuth (III) oxide and a bismuth (III) compound comprising at least one organic group which includes 2 to 20 carbon atoms; elemental sulfur; and a compound with relatively high water solubility, that makes the composition alkaline when exposed to water vapor at an elevated temperature; wherein when the composition is coated on a substrate comprising a saturant and exposed to a first condition of steam at a temperature of 134° C. for 2 minutes, the composition undergoes a change in optical density resulting in an optical density of at least 0.8, and wherein when instead exposed to a second condition of steam at a temperature of 121° C. for 3 minutes, any change in optical density is at least 0.1 optical density units less than when exposed to the first condition.

In another embodiment, there is provided a chemical indicator comprising: a substrate comprising a saturant, and a chemical indicator composition coated on at least a portion of a major surface of the substrate, the composition comprising: a bismuth (III) compound selected from the group consisting of bismuth (III) oxide and a bismuth (III) compound comprising at least one organic group which includes 2 to 20 carbon atoms; elemental sulfur; and a compound with relatively high water solubility, that makes the composition alkaline when exposed to water vapor at an elevated temperature; wherein when the composition is coated on the substrate and exposed to a first condition of steam at a temperature of 134° C. for 2 minutes, the composition undergoes a change in optical density resulting in an optical density of at least 0.8, and wherein when instead exposed to a second condition of steam at a temperature of 121° C. for 3 minutes, any change in optical density is at least 0.1 optical density units less than when exposed to the first condition.

In another embodiment, there is provided an autoclave tape comprising: an autoclave tape backing substrate comprising a saturant, and a chemical indicator composition coated on at least a portion of a major surface of the autoclave tape backing substrate, the composition comprising: a bismuth (III) compound selected from the group consisting of bismuth (III) oxide and a bismuth (III) compound comprising at least one organic group which includes 2 to 20 carbon atoms; elemental sulfur; and a compound with relatively high water solubility, that makes the composition alkaline when exposed to water vapor at an elevated temperature; wherein when the composition is coated on the autoclave tape backing and exposed to a first condition of steam at a temperature of 134° C. for 2 minutes, the composition undergoes a change in optical density resulting in an optical density of at least 0.8, and wherein when instead exposed to a second condition of steam at a temperature of 121° C. for 3 minutes, any change in optical density is at least 0.1 optical density units less than when exposed to the first condition.

In another embodiment, there is provided a chemical indicator composition comprising: a bismuth (III) compound selected from the group consisting of bismuth (III) oxide and a bismuth (III) compound comprising at least one organic group which includes 2 to 20 carbon atoms; elemental sulfur; a compound with relatively high water solubility, selected from the group consisting of potassium carbonate, potassium bicarbonate, and sodium phosphate, that makes the composition alkaline when exposed to water vapor at an elevated temperature.

In another embodiment, there is provided a chemical indicator comprising: a substrate and a chemical indicator composition coated on at least a portion of a major surface of the substrate, the composition comprising: a bismuth (III) compound selected from the group consisting of bismuth (III) oxide and a bismuth (III) compound comprising at least one organic group which includes 2 to 20 carbon atoms; elemental sulfur; a compound with relatively high water solubility, selected from the group consisting of potassium carbonate, potassium bicarbonate, and sodium phosphate, that makes the composition alkaline when exposed to water vapor at an elevated temperature.

In another embodiment, there is provided an autoclave tape comprising: an autoclave tape backing substrate and a chemical indicator composition coated on at least a portion of a major surface of the autoclave tape backing substrate, the composition comprising: a bismuth (III) compound selected from the group consisting of bismuth (III) oxide and a bismuth (III) compound comprising at least one organic group which includes 2 to 20 carbon atoms; elemental sulfur; a compound with relatively high water solubility, selected from the group consisting of potassium carbonate, potassium bicarbonate, and sodium phosphate, that makes the composition alkaline when exposed to water vapor at an elevated temperature.

In another embodiment, there is provided a chemical indicator composition comprising: a bismuth compound; a sulfur compound or elemental sulfur; a reducing agent; and a compound which makes the composition alkaline when exposed to water vapor at an elevated temperature.

In another embodiment, there is provided a chemical indicator comprising: a substrate and a chemical indicator composition coated on at least a portion of a major surface of the substrate, the composition comprising: a bismuth compound; a sulfur compound; a reducing agent; and a compound which makes the composition alkaline when exposed to water vapor at an elevated temperature.

In another embodiment, there is provided an autoclave tape comprising: an autoclave tape backing substrate and a chemical indicator composition coated on at least a portion of a major surface of the autoclave tape backing substrate, the composition comprising: a bismuth compound; a sulfur compound; a reducing agent; and a compound which makes the composition alkaline when exposed to water vapor at an elevated temperature.

In another embodiment, there is provided a method of determining the effectiveness of a steam sterilization process, the method comprising: providing any one of the above chemical indicators and/or autoclave tapes; placing the chemical indicator and/or autoclave tape in a steam sterilization chamber; exposing the chemical indicator and/or autoclave tape to steam at a temperature of at least 121° C.; and determining an optical density of the chemical indicator and/or autoclave tape.

For certain embodiments, including the above embodiments where the composition includes at least one reducing agent and/or at least one compound with relatively high water solubility that makes the composition alkaline on exposure to water vapor at an elevated temperature, the bismuth compound is an inorganic bismuth compound, an organic bismuth compound, or a combination thereof. For certain of these embodiments, the inorganic bismuth compound is selected from the group consisting of bismuth (III) oxide, bismuth subcarbonate, bismuth borate, bismuth titanate, bismuth molybdate, bismuth phosphate, and bismuth oxychloride. For certain of these embodiments, the organic bismuth compound is a bismuth (III) compound comprising at least one organic group which includes 2 to 20 carbon atoms. Alternatively, for certain of these embodiments, the bismuth compound is a combination of the organic bismuth compound and the inorganic bismuth compound.

For certain embodiments, including any one of the above composition and indicator embodiments, the bismuth (III) compound is a bismuth (III) compound comprising at least one organic group which includes 2 to 20 carbon atoms. For certain of these embodiments, the bismuth (III) compound is selected from the group consisting of bismuth subsalicylate (CAS Reg. No. 14882-18-9), bismuth gallate (3,4,5-trihydroxybenzoic acid bismuth salt, CAS Reg. No. 57206-57-2), bismuth subgallate (2,7-dihydroxy-1,3,2-benzodioxabismol-5-carboxylic acid, CAS Reg. No. 99-26-3), bismuth pyrogallate (1,2,3-benzenetriol, bismuth salt, basic, CAS Reg. No. 12001-49-9), bismuth acetate (bismuth triacetate, CAS Reg. No. 22306-37-2), bismuth citrate (CAS Reg. No. 110230-89-2), bismuth potassium citrate (CAS Reg. No. 57644-54-9), ammonium bismuth citrate (CAS Reg. No. 67953-07-5), bismuth lactate (CAS Reg. No. 6591-53-3), bismuth oxalate (CAS Reg. No. 6591-55-5), bismuth benzoate, bismuth formate, bismuth propionate, bismuth butyrate, bismuth pivalate (bismuth salt of 2,2-dimethylpropanoic acid), 2-propylpentanoic acid bismuth salt (CAS Reg. No. 94071-09-7), bismuth ascorbate, bismuth diethyldithiocarbamate (tris(diethyldithiocarbamato) bismuth (III), CAS Reg. No. 20673-31-8), bismuth dimethyldithiocarbamate, bismuth 2-ethylhexanoate (CAS Reg. No. 67874-71-9), bismuth neodecanoate (CAS Reg. No. 34364-26-6), bismuth oleate, bismuth gluconate, bismuth potassium D-gluconate, bismuth naphtholate (CAS Reg. No. 8039-60-9), naphthenic acid bismuth salt (CAS Reg. No. 85736-59-0), bismuth triglycollamate, bismuth sodium triglycollamate (N,N-bis(carboxymethyl)glycine disodium salt/N-(carboxymethyl)-N-[2-oxo-2-{(oxobismuthino)oxy}ethyl]glycine monosodium salt (3:1), CAS Reg. No. 5798-43-6), bismuth succinate (CAS Reg. No. 139-16-2), bismuth maleate (CAS Reg. No. 88210-84-8), bismuth tartrate (CAS Reg. No. 6591-56-6), bismuth sodium tartrate (CAS Reg. No. 31586-77-3), bismuth potassium tartrate (CAS Reg. No. 5798-41-4), bismuth tannate, 3-camphocarboxylic acid bismuth salt (CAS Reg. No. 4154-53-4), bismuth ethylcamphorate (CAS Reg. No. 52951-37-8), bismuth oxyquinoline (CAS Reg. No. 1300-75-0), 2-oxo-3-bornanecarboxylic acid bismuth salt (CAS Reg. No. 19495-28-4), bismuth valproate, and a combination thereof. Any of the compounds having at least one chiral center includes any one of the stereoisomers or any combination thereof, including racemic mixtures. For example, bismuth gluconate includes all forms of the gluconate (e.g., D-gluconic acid bismuth (III) salt (CAS Reg. No. 94232-39-0), L-gluconic acid bismuth (III) salt, and/or a racemic mixture thereof. For certain of these embodiments, the bismuth (III) compound is selected from the group consisting of bismuth subsalicylate, bismuth subgallate, bismuth acetate, bismuth citrate, bismuth neodecanoate, and a combination thereof. For certain of these embodiments, the bismuth (III) compound is bismuth subsalicylate.

For certain embodiments, including any one of the above composition and indicator embodiments, except where the bismuth (III) compound is a bismuth (III) compound comprising at least one organic group which includes 2 to 20 carbon atoms, the bismuth (III) compound is bismuth (III) oxide.

Elemental sulfur is known to exist as an eight membered ring of sulfur atoms. Under certain alkaline conditions, for example, in the presence of a nucleophile, such as hydroxide ion, the ring of sulfur atoms can be opened and sulfide ions can be formed from the resulting chain of sulfur atoms. In the presence of the sulfide ions, the bismuth compound can form bismuth sulfide, which is dark in color. Additionally, under certain reducing conditions, for example, in the presence of a reducing agent such as an ascorbate, the ring of sulfur atoms can be opened and sulfhydryl groups can be formed, and under basic conditions, the sulfhydryl groups can be converted to sulfide ions that can react with the bismuth compound to form bismuth sulfide which is dark in color.

For certain embodiments, other sulfur compounds can be used. For example, disulfides; thioureas, such as N,N-diphenylthiourea; and thiocarbamates, as well as dithiocarbamates, can be used as the sulfur source. Additionally, sulfide salts, such as calcium sulfide and potassium sulfide can be used as the sulfur source for certain embodiments.

The compound with relatively high water solubility that makes the composition alkaline when exposed to water vapor at an elevated temperature is believed to bring about conditions whereby sulfide ions are formed. Compounds suitable for this purpose include, for example sodium carbonate, sodium bicarbonate, potassium carbonate, potassium bicarbonate, sodium phosphate, and the like. Compounds with relatively high water solubility that make the compositions alkaline when exposed to water vapor at elevated temperatures are believed to increase the concentration of sulfide ions in the indicator compositions during steam sterilization cycles, thus effecting a greater yield of dark bismuth sulfide than generators of alkaline conditions that are only slightly water soluble. On the one hand, compounds which have a relatively high solubility in water previously had been found to cause the compositions and indicators to darken prematurely or earlier than desired during exposure to steam sterilization process conditions. In addition, this can cause the optical density of the composition after exposure to a steam sterilization process condition known to be insufficient for bringing about sterilization to be undesirably similar to the optical density of the composition after exposure to a sterilization effective condition.

On the other hand, compounds with low water solubility had been found to be less desirable due to level of darkness after exposure to steam sterilization process conditions, particularly in embodiments of indicators that contain saturants. In addition, this can cause the optical density of the composition after exposure to a steam sterilization process condition to be insufficient for indicating exposure to a sterilization effective condition.

Autoclave tape typically contains a paper substrate that is strengthened by means of a saturant. In the case of a rubber or rubber-like saturant, the reaction medium for reaction of a bismuth compound to form a black product upon exposure to steam is a non-polar organic environment that is relatively resistant to permeation by water (from steam). Thus, while bismuth subcarbonate and bismuth subsalicylate-comprising inks give a color change to black on adequate exposure to steam on substrates that do not include a saturant, they give a light brown color on adequate exposure to steam on substrates that include a saturant. This is believed to be due to the reduced solubility, and thus reduced reactivity, of these inorganic compounds in the saturant-containing tape as well as the relative resistance to permeation of the saturant to steam.

While use of the ink formulations disclosed in U.S. Pat. No. 5,916,816 and PCT Application No. PCT/US2009/069815, filed Dec. 30, 2009 for autoclave tape is possible, the typically brown (rather than black) color of the ink on exposure to adequate steam obtained in a saturant-containing tape format using those disclosed inks is less than optimal. Additionally, it has been found that preferences for color change characteristics of autoclave tapes and other chemical indicators vary by end-user (e.g., a hospital), so while a dark brown color change after exposure to steam may be acceptable to one end-user, only a change to black on exposure to steam may be acceptable to another end-user. What is needed, then, is a lead-free ink suitable for use in an autoclave tape that indicates the presence of steam by a color change to black.

Accordingly, for certain embodiments, including any one of the indicator composition, indicator and method embodiments described herein, the compound that makes the indicator composition alkaline has a solubility in water at 20° C. of preferably more than about 5 grams per 100 cubic centimeters (ml) of water; more preferably, a solubility in water at 20° C. of more than about 8 grams per 100 cubic centimeters (ml) of water; and even more preferably, a solubility in water at 20° C. of at least about 10 grams per 100 cubic centimeters (ml) of water.

In many embodiments, the relatively high solubility compound that makes the indicator composition alkaline is selected from the group consisting of sodium carbonate, sodium bicarbonate, potassium carbonate, potassium bicarbonate, and sodium phosphate, or combinations thereof. For certain of these embodiments, the relatively high solubility compound that makes the indicator composition alkaline is selected from the group consisting of potassium carbonate, potassium bicarbonate, and sodium phosphate, or a combination thereof. For certain of these embodiments, the compound that makes the indicator composition alkaline is potassium bicarbonate or sodium bicarbonate. For the indicator compositions of the present disclosure, the compound that makes the composition alkaline on exposure to water vapor at elevated temperature and that has relatively high water solubility is present in the composition, preferably, at between 0.5 wt % and 4.0 wt %, based on the total weight of the composition; and more preferably, between 1.0 wt % and 2.5 wt %, based on the total weight of the composition.

As illustrated in the examples, inclusion of one or more compound in the indicator composition that makes the composition alkaline when exposed to water vapor at elevated temperature and that has relatively low water solubility is also useful, in combination with the other components (e.g., the relatively high water solubility compound, and/or the reducing agent). For example, lithium carbonate has been found useful as a compound that makes the indicator composition alkaline when exposed to water vapor at elevated temperature and that has relatively low water solubility. While the addition of lithium carbonate and other compounds with low water solubility that make the indicator compositions alkaline on exposure to water vapor at elevated temperature (e.g., in steam) does not lead to autoclave tape indicators that turn black upon exposure to steam, the addition of lithium carbonate and the like can reduce the amount of relatively highly water soluble compounds (such as sodium carbonate and the like) needed in other indicator compositions, for example, in indicator compositions used in chemical indicators that do not utilize saturant.

Without being bound by theory, it is believed that the reducing agent when present in the indicator compositions, and/or when combined with a compound that makes the composition alkaline in the presence of water vapor at elevated temperature, facilitates formation of sulfide groups that react with the bismuth compound to darken the color of the indicator composition upon exposure to steam. Useful reducing agents include ascorbic acid and its derivatives, tocopherols, bisulfites (such as sodium bisulfite), thiosulfates, gallates (such as propyl gallate), t-butyl hydroquinones (such as t-butyl hydroquinone), napthylamines (such as Irganox L-06), polyphenols (such as Irganox L-101), and combinations thereof.

One class of reducing agents that may be useful includes ascorbic acid and its derivatives. For example, ascorbic acid, or the ascorbate salts (such as sodium ascorbate or potassium ascorbate), may be used. Esters of ascorbic acid may also be useful, such as ascorbyl palmitate. For indicator compositions of the present disclosure, the reducing agent is preferably present at between 1 and 5 weight percent of the composition.

For certain embodiments, including any one of the above composition and indicator embodiments, the composition further comprises a binder. The binder holds the composition in place when coated on a substrate. Preferably the binder comprises a film-forming material, which is stable to heat and water vapor. A film formed by the binder is sufficiently permeable to water vapor and steam to allow a desired color change to occur under sterilization conditions. Materials that the binder may comprise include, for example, acrylate and methacrylate polymers and copolymers (e.g., poly(methylmethacrylate) and methyl/n-butyl methacrylate copolymer), poly(vinyl acetate) and poly(vinylchloride) and copolymers thereof, and various derivatives of cellulose, including, for example, ethylcellulose and nitrocellulose. In certain embodiments, the binder may be an ultraviolet light-, visible light-, or thermally-curable material. Preferably, such materials are used without solvent.

It has been found that compositions comprising a sufficiently acidic binder can provide a significant increase in the difference between the optical density after exposure to steam at 132° C. for 2.5 minutes and 134° C. for 3.5 minutes. A Class 4 chemical indicator wherein indications of pass and fail can be more readily and reliably distinguished can, therefore, be provided. Accordingly, for certain embodiments, including any one of the above composition and indicator embodiments, the binder comprises a polymer comprising acid groups, wherein the binder has an acid number of at least 7. For certain of these embodiments, the binder comprises an acrylate polymer, a methacrylate polymer, an acrylate copolymer, a methacrylate copolymer, an acrylate/methacrylate copolymer, or a combination thereof, wherein the polymer or copolymer comprises sufficient carboxylic acid groups for an acid number of at least 7. For certain of these embodiments, preferably the acid number is at least 8 or at least 9. For certain of these embodiments, the binder comprises a methyl/n-butyl methacrylate copolymer.

Compositions and indicators described herein provide good optical density differentiation between fail and pass steam sterilization conditions. For example, the optical density of a composition exposed to steam at 134° C. for 0.5 minutes or steam at 121° C. for 3 minutes (which are considered to be fail steam sterilization conditions for an ISO 11140 Class 1 indicator) can be clearly seen to be lower than when the composition is exposed to steam at 134° C. for 2.0 minutes or steam at 121° C. for 10 minutes (which may be considered to be pass steam sterilization conditions for an ISO 11140 Class 1 indicator).

Suitable chemical indicator compositions have a visually and/or measurably significant difference in optical density between steam at 134° C. for 2.0 minutes (the pass steam sterilization conditions for an ISO 11140 Class 1 indicator), and steam at 121° C. for 3 minutes (the fail steam sterilization conditions for an ISO 11140 Class 1 indicator). These two cycles typically constitute the two steam exposure conditions that give the narrowest difference in optical densities. A measurably significant difference in optical density is 0.1, for example, at these two conditions.

For certain embodiments, including any one of the above described composition and indicator embodiments, when exposed to a first condition of steam at a temperature of 134° C. for 2 minutes, the composition undergoes a change in optical density resulting in an optical density of at least 0.8, more preferably 0.9, and wherein when instead exposed to a second condition of steam at a temperature of 121° C. for 3 minutes, any change in optical density is at least 0.1 optical density units less than when exposed to the first condition and preferably is at least 0.2 optical density units less than when exposed to the first condition.

Not only can compositions and indicators described herein provide good optical density differentiation between fail and pass steam sterilization conditions, but a darker color can be achieved when exposed to a pass steam sterilization condition. For certain embodiments, including any one of the above composition and indicator embodiments, when exposed to a first condition of steam at a temperature of 134° C. for 2 minutes, the composition changes color to brown or black. In preferred embodiments, including any one of the above composition and indicator embodiments, when exposed to a first condition of steam at a temperature of 134° C. for 2 minutes, the composition changes color to black.

For certain of these embodiments, when exposed to the first condition the composition undergoes a change in optical density resulting in an optical density of at least 0.9, and wherein the first condition is steam at a temperature of 134° C. for 2 minutes. A Class 1 chemical indicator wherein indications of pass and fail can be more readily and reliably distinguished can, thereby, be provided.

Relatively low ratios of bismuth to the other components in the compositions have been found to be effective in providing the desired properties described herein. As a result, the amounts of bismuth used in the compositions and indicators described herein can be reduced relative to previously known chemical indicator compositions. For certain embodiments, including any one of the above composition and indicator embodiments, the bismuth (III) compound and the elemental sulfur are present in the composition in a weight ratio of not more than 2:3 and not less than 0.5:3; and wherein the elemental sulfur and the compound that makes the composition alkaline are present in a weight ratio of not more than 20:1 and not less than 2:1.

Compositions described herein may also include a solvent for dispersing the various components of the composition, and in certain embodiments, preferably for dissolving the binder. Suitable solvents include alcohols, esters, ketones, and aromatic hydrocarbons. For certain embodiments, the solvent is preferably selected from the group consisting of n-propyl acetate, n-propyl alcohol, methanol, ethanol, 2-ethoxyethanol, butyl acetate, n-butanol, toluene, cyclohexanone, and a combination thereof. The compositions may be provided as chemical indicator inks, or the compositions may be coated onto a substrate and any solvent present evaporated, for example, by heating in an oven to provide a chemical indicator.

The compositions may include other additives, such as defoamers, flow aids, fillers, plasticizers, surfactants, and the like, so that when coated the compositions provide coatings having desirable properties. Such properties include uniform thickness, desired surface properties (glossy surface, mat surface, or the like), sufficient flexibility for bending without cracking, a particular starting color prior to exposure to steam sterilization process conditions, and the like, and combinations thereof.

As mentioned above, the color of the steam-exposed (using an ISO 11140 "pass" cycle or AMSCO steam sterilizer cycle of 132° C. for about 3-4 minutes) lead-free chemical indicator composition of the present disclosure is black. The binder identity, the ratio of bismuth compound to sulfur, the presence or absence of highly water-soluble compounds capable of making the indicator composition alkaline on exposure to water vapor at elevated temperatures, and the presence or absence of reducing agents, can all affect the final color change of the lead-free chemical indicators on exposure to steam.

Noting that some customers prefer the color change endpoint of a steam sterilization indicator to be black rather than brown, the inventors recognized that further addition of various dyes or pigments to the lead-free ink formulations described herein can effect a color change to black even when the ink formulation without added dye changes to brown. The dyes and pigments useful in the present disclosure may be any dye or pigment (or combination of dyes, pigments, or of dyes and pigments) that provides an acceptable color for the chemical indicator composition prior to exposure to steam and that adds to the color of the steam-exposed indicator composition to provide a black color on exposure to steam. For example, addition of the blue dye, Hostaperm Blue, at final concentration of 0.05% liquid ink causes the original color of the ink to be pale green, rather than white, but effects a color change to black, rather than brown, after exposure to steam. Further, a combination of a blue pigment or dye and a yellow pigment or dye gives a chemical indicator composition that is green prior to exposure to steam and that provides for a black color change on exposure to steam when used in indicator compositions that otherwise turn brown on exposure to steam.

Other dyes can be used provided they are soluble in the solvent system employed. To determine whether a dye used to obtain a black color when a brown color is normally obtained, the dye is dissolved in finished ink, mixed, coated onto substrate, exposed to steam for a desired steam sterilization cycle, and the original color and the final color are compared (e.g., brown to black).

Water-soluble dyes are often a different color (or are essentially colorless) when dispersed in organic solvents than they are when they are dissolved in water. Thus, water-soluble dyes are available that can be dispersed in the ink formulations of the present disclosure and will not change the original color of the ink substantially but will effect a black color change upon exposure to steam. Upon exposure, the water-soluble dye dissolves, becomes colored, and complements the brown color change of the indicator composition without added dye to provide a black appearance.

PH-indicating dyes are suitable for effecting a color change to black when the chemical indicator composition inherently turns brown. For example, bromocresol purple sodium salt, when added to an ink formulation at 0.01% of liquid ink, does not change substantially the color of the original printed ink, but effects a black color change on exposure to steam. Other pH indicators, such as bromothymol blue and phenol red, are suitable for the same purpose. While not intending to be bound, it is believed that the original color of the ink is not affected since the water-soluble pH indicator does not contact water during mixing of the dye with the chemical indicator ink solution that contains an organic solvent, such as alcohol solvents. Upon exposure to steam, however, and in the presence of base (e.g., lithium carbonate, sodium carbonate), the pH indicator dissolves and changes color, the final color of which, if complementary to brown, results in a black color change.

For certain embodiments, including any one of the chemical indicator composition embodiments, any one of the chemical indicator embodiments, or any one of the method embodiments described herein, the chemical indicator composition further comprises a dye which causes the color of the composition in the presence of steam to become black; wherein without the dye, the color of the composition in the presence of steam would be brown.

As indicated above, the present disclosure also provides a method of determining the effectiveness of a steam sterilization process, the method comprising providing a chemical indicator according to any one of the indicator embodiments described above; placing the chemical indicator in a steam sterilization chamber; exposing the chemical indicator to steam at a temperature of at least 121° C.; and determining an optical density of the chemical indicator. The indicators described herein produce a significantly increased optical density when exposed to a steam sterilization process condition classified as a pass condition. When exposed to a steam sterilization process condition classified as a fail condition, any increase in optical density produced by the indicator is readily discerned from that produced by the pass condition.

For certain embodiment of the above method, the method further comprises placing an article to be sterilized along with the sterilization process indicator in the sterilization chamber. The article is then exposed to the same sterilization conditions as the chemical indicator.

For certain embodiments, including any one of the above method embodiments, the method further comprises determining whether or not sterilization conditions were met in the sterilization chamber. For example, upon exposure to sterilization conditions targeted for 121° C. for 10 minutes, these sterilization conditions are determined to have been met when the chemical indicator produces an optical density in a range known to indicate exposure to these conditions. On the other hand, when exposed to inadequate sterilization conditions the chemical indicator produces an optical density below an optical density range known to be produced by the indicator at 121° C. for 10 minutes, and sterilization conditions are determined not to have been met. The characteristics of the compositions and indicators described above make determining whether or not sterilization conditions were met in the sterilization chamber easier and more reliable.

As indicated above, the chemical indicators described herein include a substrate. The substrate may be any substrate that remains intact and does not degrade when subjected to steam sterilization process conditions. Suitable substrates include paper without or with a saturant (e.g., rubber, natural or synthetic latex, a polymer, or the like), coated paper, cardboard, plastic sheeting, metalized sheeting, metal foil, non-woven or woven fabrics, and the like.

Other embodiments in which the compositions and methods described herein may be useful are described in Applicants' co-pending PCT Application No. PCT/US2009/069815, filed Dec. 30, 2009, which is incorporated by reference herein in its entirety.

For most embodiments, including any one of the above chemical indicator embodiments and any one of the method embodiments, the substrate of the chemical indicator and/or tape is impregnated with a saturant.

For certain embodiments, including any one of the above chemical indicator embodiments and any one of the method embodiments, the substrate of the chemical indicator further includes a barrier layer, and the chemical indicator composition is coated on the barrier layer. For certain of these embodiments, the chemical indicator further comprises a low adhesion back-size layer covering the barrier layer and covering the chemical indicator composition coated on the barrier layer. Alternatively, the chemical indicator further comprises a barrier layer covering the major surface of the substrate and covering the chemical indicator composition coated on the at least a portion of the major surface of the substrate. For certain of these embodiments, the chemical indicator further comprises a low adhesion back-size layer covering the barrier layer.

For certain embodiments, including any one of the above chemical indicator embodiments and any one of the method embodiments, the chemical indicator further comprises an adhesive layer on the major surface of the substrate opposite the major surface of the substrate upon which the chemical indicator composition is coated.

For certain embodiments, including any one of the above chemical indicator embodiments and any one of the method embodiments, the chemical indicator is a tape.

For certain embodiments, the substrate is in the form of a tape. In one example, preferably the tape is comprised of a pressure sensitive adhesive on one side and any one of the composition embodiments described above on the opposite side. Preferably the tape is provided in roll form.

Referring to FIG. 1, in one embodiment, chemical indicator tape 100 is illustrated in cross-section. Substrate 110 is coated with chemical indicator composition 140 on a portion of a first major surface and has adhesive layer 120 covering at least a portion of the major surface on the side of substrate 110 opposite composition 140. Substrate 110 is preferably a paper, for example, kraft paper or crepe paper impregnated with a saturant. Chemical indicator tape 100 illustrated in FIG. 1 further includes saturant layer 150 covering composition 140, optional barrier layer 170 covering substrate 110 and saturant layer 150, and optional low adhesion backsize layer 190 covering barrier layer 170.

Chemical indicator composition 140 may be any one of the composition embodiments described herein. For certain embodiments, composition 140 is coated on substrate 110 by printing a chemical indicator composition described herein in the form of an ink. Substrate 110 is preferably a paper, for example, kraft paper or crepe paper impregnated with a saturant. Saturants sufficiently resistant to steam may be used, for example, natural rubber and/or polymerized rosins without or with a pigment, for example zinc oxide and/or titanium oxide; styrene-butadiene polymers without or with rosin; acrylic polymer; a combination of acrylic polymer, styrene-butadiene polymer, and acrylonitrile polymer, and n-butyl acrylate-acrylonitrile-styrene terpolymer. The adhesive layer is preferably a water resistant pressure sensitive adhesive (PSA). PSAs that may be used for the adhesive layer include, for example, cross-linked acrylics, tackified rubber adhesives, for example, natural rubber, polyisoprene, styrene butadiene rubber, and the like.

Chemical indicator tape 100 illustrated in FIG. 1 further may optionally include barrier layer 170 covering substrate 110 and chemical indicator composition 140. Low adhesion backsize layer 190 may also be used to cover barrier layer 170. Materials that may be used for the barrier layer include, for example, acrylic polymers, urea-formaldehyde compositions, styrene butadiene rubbers, cellulose acetate, cellulose acetate propionate, cellulose acetate butyrate, ethyl cellulose, non-drying coconut oil alkyd, and acrylic modified alkyd. Materials that may be used for the low adhesion backsize layer or release layer include, for example, acrylic, urethane, and silicone polymers.

Compositions described herein can be conveniently prepared by mixing the components of the binder, a solvent, the bismuth compound, the elemental sulfur, the compound (e.g., with relatively high water solubility) that makes the composition alkaline when exposed to water vapor at an elevated temperature, a reducing agent, if desired, and pigment(s) and/or dye(s), if desired. The mixing can be carried out using known mixing processes. In one example, the mixing is carried out in a ball mill wherein the particle size of the insoluble components (e.g., elemental sulfur, the compound that makes the composition alkaline, the bismuth compound) is reduced and the particles are dispersed. The binder and the solvent together may comprise about 50 to 97 percent by weight of the composition, and the elemental sulfur, the compound that makes the composition alkaline, and the bismuth compound in combination may comprise about 3 to about 50 percent by weight, preferably about 20 to about 25 percent by weight of the composition.

Compositions described herein may be coated onto the substrate using a variety of known coating methods including by a wire-wound rod (i.e., Meyer bar or Mayer rod) and various printing methods, including, for example, flexographic, rotogravure, and screen printing. The compositions may be applied in a pattern, for example, stripes, chevrons, or the like, to provide a visual contrast between areas of the indicator that will provide a color change after exposure to steam sterilization conditions and background areas of the indicator. Alternatively, the indicator may be coated without a pattern, such as by web coating techniques.

More than one substrate may be used in an indicator to provide desirable optical densities for use in multiple sterilization process conditions and for use as multiple classes of chemical indicators. Likewise, more than one composition may be coated and used in an indicator for the same purpose.

For certain embodiments, a film can be laminated onto the coated composition. Preferably the film is permeable to steam, although in certain embodiments steam may contact the coated composition through the substrate upon which the composition is coated.

Optical densities of the compositions are measured after the composition is coated onto a substrate and any solvent evaporated from the composition. Known devices for measuring optical densities of a surface may be used, such as a spectrodensitometer.

Objects and advantages of various embodiments of the present disclosure are further illustrated by the following examples, but the particular materials and amounts thereof recited in these examples, as well as other conditions and details, should not be construed to unduly limit this invention.

EXAMPLES

TABLE 1

Example Components

| Component | Supplier, location |
|---|---|
| Tape backing (29 lb., "2164" Calendered, Smooth Crepe, Semi-bleached Kraft Saturating Paper, Reverse Wound, 49.25" (1251 mm) wide, | Wausau Paper, Wausau, WI |
| L-Ascorbic Acid | MC-B, Norwood, OH |
| Ascorbyl palmitate | Alfa Aesar, Ward Hill, MA |
| Bismuth subsalicylate | Alfa Aesar, Ward Hill, MA |
| t-butyl hydroquinone | Eastman Kodak, Rochester, NY |
| Calcium carbonate | EMD, Gibbstown, NJ |
| Calcium hydroxide | JT Baker, Phillipsburg, NJ |
| Ethocel 7 Industrial (ethyl cellulose) | Dow Chemical, Midland, MI |
| Irganox L-06 and Irganox L-101 | Ciba Specialty Chemicals, (BASF), Tarrytown, NY |
| Lithium carbonate | FMC Lithium Division, Bessemer, NC |
| Potassium bicarbonate | JT Baker, Phillipsburg, NJ |
| Potassium carbonate anhydrous | Sigma-Aldrich, St. Louis, MO |
| n-propyl acetate | Brenntag, Milwaukee, WI |
| n-propyl alcohol | Brenntag, Milwaukee, WI |
| n-propyl gallate | Sigma-Aldrich, St. Louis, MO |
| Sodium bicarbonate | Fisher Scientific, Fair Lawn, NJ |
| Sodium Bisulfite | VWR, West Chester, PA |
| Sodium carbonate anhydrous | Mallinckrodt Chemicals, Phillipsburg, NJ |
| Sodium phosphate tribasic | Fisher Scientific, Fair Lawn, NJ |
| Sulfur | Akrochem, Akron, OH |
| Alpha-tocopherol | Sigma-Aldrich, St. Louis, MO |
| Zinc carbonate | Fisher Scientific, Fair Lawn, NJ |

Preparation of Binder Stock Solution

The binder solution was prepared by mixing 100 g ethyl cellulose (Ethocel, Dow Chemical, Midland, Mich.) with 261.6 g n-propyl acetate and 175.4 g n-propyl alcohol. The mixture was rolled overnight in a jar to give a homogeneous solution.

Preparation and Use of Rubber Saturant

A rubber saturant composition was prepared with the following ingredients: 23% natural rubber; 6% zinc oxide; 2.5% titanium dioxide; 29% wood-rosin; 2.5% aromatic resin; and 37% mineral spirits Immediately prior to saturating the ink-coated backing of each example, 15.0 grams of rubber saturant was mixed with 1.23 grams of a solution of vulcanizing accelerants and stirred by hand for 3 minutes. The accelerator solution contains 30 grams of xylene (VWR, West Chester, Pa.), 2.98 grams of Robac P25 (dipentamethylene thiuram polysulfide, Robinson Brothers, West Midlands, UK) and 1.0 gram of methyl tuads (tetramethylthiuram disulfide, R. T. Vanderbilt, Norwalk, Conn.).

Examples 1A-1D

Indicator Tapes with Bismuth Subsalicylate and Sodium Carbonate

The ingredients in Table 2, for Examples 1A-1D, were placed into 120 mL (4 oz) glass jars with 20 glass marbles of diameter 12.7 mm (½ inch). The mixtures were rolled on a ball roller for 16 hours and then coated onto tape backing using a #16 Mayer Rod. The coatings were dried for 5 minutes at 50° C. The coated tape backing samples were saturated by applying a few milliliters of the rubber saturant (above), containing vulcanizing accelerants, to both major surfaces of each tape backing using a plastic squeegee, followed by curing at 140° C. for 3 minutes. After curing, each tape backing was exposed to steam in an AMSCO EAGLE 3013C sterilizer using a prevac cycle at 132° C. for 3 minutes with a 1 minute drying period. Optical densities were measured using an X-Rite 530P spectrodensitometer.

TABLE 2

Comparison of Indicator Tape compositions with and without Na$_2$CO$_3$

| Ingredient | Ex. 1A* grams | Ex. 1B grams | Ex. 1C grams | Ex. 1D grams |
|---|---|---|---|---|
| Bismuth subsalicylate | 1.18 | 1.18 | 1.18 | 1.18 |
| Sulfur | 3.61 | 3.61 | 3.61 | 3.61 |
| Lithium carbonate | 9.58 | 9.58 | 9.58 | 9.58 |
| Sodium carbonate | 0 | 0.40 | 1.54 | 6.70 |
| Binder solution | 25.63 | 25.23 | 24.09 | 18.9 |
| Optical Density | 0.74 | 0.87 | 0.91 | 0.98 |

*Example 1A is a comparative example.

The results indicate that the optical density of the indicators on exposure to steam increases as the weight percentage of sodium carbonate, a compound with high water solubility, is increased.

Examples 2A-2C and 2D-2J

Bismuth Subsalicylate Combined with Reducing Agents and Sodium Carbonate

The ingredients in Table 3, for Examples 2A-2C, and the ingredients in Table 4 for examples 2D-2J, were placed into 120 mL (4 oz) glass jars with 20 glass marbles of diameter 12.7 mm (½ inch). The mixtures were rolled on a ball roller for 16 hours and then coated onto tape backing using a #16 Mayer Rod. The coatings were dried for 5 minutes at 50° C. The coated tape backing samples were saturated by applying a few milliliters of the rubber saturant (above), containing vulcanizing accelerants, to both major surfaces of each tape backing using a plastic squeegee, followed by curing at 140° C. for 3 minutes. After curing, each tape backing was exposed to steam in an AMSCO EAGLE 3013C sterilizer using a prevac cycle at 132° C. for 3 minutes with a 1 minute drying period for Examples 2A-2C. For Examples 2D-2J, after curing, each tape backing was exposed to steam in an AMSCO EAGLE 3013C sterilizer using a prevac cycle at 132° C. for 4 minutes with a 1 minute drying period. Other prepared Examples 2D-2J were exposed to steam in a Joslyn resistometer (available from Joslyn Sterilizer Corporation of Farmington, N.Y.) using one of the cycles shown in Table 5. Optical densities were measured using an X-Rite 530P spectrodensitometer.

TABLE 3

Comparison of indicator compositions with and without reducing agents

| Ingredient | Ex. 2A grams | Ex. 2B grams | Ex. 2C grams |
|---|---|---|---|
| Bismuth subsalicylate | 1.18 | 1.18 | 1.18 |
| Sulfur | 3.61 | 3.61 | 3.61 |
| Lithium carbonate | 4.79 | 4.79 | 4.79 |
| Sodium carbonate | 0.6 | 0.6 | 0.6 |

TABLE 3-continued

Comparison of indicator compositions with and without reducing agents

| Ingredient | Ex. 2A grams | Ex. 2B grams | Ex. 2C grams |
|---|---|---|---|
| Ascorbyl palmitate | 0 | 0 | 0.4 |
| Ascorbic acid | 0 | 0.4 | 0 |
| Binder solution | 29.82 | 29.42 | 29.42 |
| Total | 40 | 40 | 40 |
| Optical Density | 0.71 | 0.82 | 0.81 |

The optical density results of Examples 2B and 2C, Table 3, show that the reducing agents, ascorbyl palmitate and ascorbic acid, increase the optical density of the indicators upon adequate exposure to steam when compared with the control Example 2A, which does not contain a reducing agent.

TABLE 4

Comparison of Indicator compositions with and without reducing agents

| Ingredient | 2D grams | 2E grams | 2F grams | 2G grams | 2H grams | 2I grams | 2J grams |
|---|---|---|---|---|---|---|---|
| Bismuth subsalicylate | 1.18 | 1.18 | 1.18 | 1.18 | 1.18 | 1.18 | 1.18 |
| Sulfur | 3.61 | 3.61 | 3.61 | 3.61 | 3.61 | 3.61 | 3.61 |
| Lithium carbonate | 4.79 | 4.79 | 4.79 | 4.79 | 4.79 | 4.79 | 4.79 |
| Ascorbyl palmitate | 0.4 | 0 | 0 | 0 | 0 | 0 | 0 |
| Sodium bisulfite | 0 | 0.4 | 0 | 0 | 0 | 0 | 0 |
| Alpha-tocopherol | 0 | 0 | 0.4 | 0 | 0 | 0 | 0 |
| Irganox L-06 | 0 | 0 | 0 | 0.4 | 0 | 0 | 0 |
| t-butyl hydroquinone | 0 | 0 | 0 | 0 | 0.4 | 0 | 0 |
| n-propyl gallate | 0 | 0 | 0 | 0 | 0 | 0.4 | 0 |
| Irganox L-101 | 0 | 0 | 0 | 0 | 0 | 0 | 0.4 |
| Binder solution | 30.02 | 30.02 | 30.02 | 30.02 | 30.02 | 30.02 | 30.02 |
| Total | 40 | 40 | 40 | 40 | 40 | 40 | 40 |

TABLE 5

Optical Density results of Indicator Tape compositions with and without reducing agents

| Steam Exposure | 2D | 2E | 2F | 2G | 2H | 2I | 2J |
|---|---|---|---|---|---|---|---|
| AMSCO 132° C., 4 min | 1.12 | 1.19 | 1.07 | 1.02 | 1.05 | 1.00 | 1.05 |
| color after AMSCO | black | black | black | black | black | black | black |
| Resistometer 134° C., 2 min | 0.92 | 1.05 | 0.77 | 0.75 | 0.83 | 0.78 | 0.67 |
| Resistometer 134° C., 30 sec | 0.41 | 0.66 | 0.28 | 0.22 | 0.31 | 0.34 | 0.22 |
| Resistometer 121° C., 10 min | 1.01 | 0.99 | 0.91 | 0.86 | 0.94 | 0.83 | 0.83 |
| Resistometer 121° C., 3 min | 0.61 | 0.77 | 0.47 | 0.39 | 0.55 | 0.52 | 0.39 |
| OD difference between 134° C., 2 min and 121° C., 3 min cycles | 0.31 | 0.28 | 0.44 | 0.47 | 0.39 | 0.31 | 0.44 |

The results of Examples 2D through 2J, Table 5, show that reducing agents increase the optical density of the indicators upon adequate exposure to steam compared with the control Example 1A.

Examples 3A-3C

Bismuth Subsalicylate with Sodium Carbonate and Ascorbic Acid

The ingredients in Table 6, for examples 3A-3C, were placed into 120 mL (4 oz) glass jars with 20 glass marbles of diameter 12.7 mm (½ inch). The mixtures were rolled on a ball roller for 16 hours and then coated onto tape backing using a #16 Mayer Rod. The coatings were dried for 5 minutes at 50° C. The coated tape backing samples were saturated by applying a few milliliters of the rubber saturant (above), containing vulcanizing accelerants, to both major surfaces of each tape backing using a plastic squeegee, followed by curing at 140° C. for 3 minutes. After curing, each tape backing was exposed to steam in an AMSCO EAGLE 3013C sterilizer using a prevac cycle at 132° C. for 3 minutes with a 1 minute drying period. Optical densities were measured using an X-Rite 530P spectrodensitometer.

TABLE 6

Indicator Tape compositions with different amounts of ascorbic acid

| Ingredient | Ex. 3A grams | Ex. 3B grams | Ex. 3C grams |
|---|---|---|---|
| Bismuth subsalicylate | 2.36 | 2.36 | 2.36 |
| Sulfur | 7.22 | 7.22 | 7.22 |
| Lithium carbonate | 4.79 | 4.79 | 4.79 |
| Sodium carbonate | 1.2 | 1.2 | 1.2 |
| Ascorbic acid | 0.8 | 1.6 | 2.4 |
| Binder solution | 63.63 | 62.83 | 62.03 |
| Optical Density | 0.82 | 0.93 | 0.98 |

The results indicate that addition of increasing amounts of ascorbic acid to the bismuth-comprising inks increases correspondingly the initial optical density of the steam-exposed indicators.

Examples 4A-4N

Bismuth Subsalicylate with Compounds that Make Indicator Compositions Alkaline on Exposure to Water Vapor at Elevated Temperature The ingredients in Table 7, for Examples 4A-4G, and the ingredients in Table 9, for Examples 4H-4N, were placed into 240 mL (8 oz) glass jars with 40 ceramic cylinders of diameter×length 12.7 mm×12.7 mm (½ inch×½ inch). The mixtures were rolled on a ball roller for 16 hours and then coated onto tape backing using a #22 Mayer Rod. The coatings were dried for 5 minutes at 50° C. The coated tape backing samples were saturated by applying a few milliliters of the rubber saturant (above), including vulcanizing accelerants, to both major surfaces of each tape backing using a plastic squeegee, followed by curing at 140° C. for 3 minutes. After curing, each tape backing was exposed to steam in an AMSCO EAGLE 3013C sterilizer using a prevac cycle at 132° C. for 4 minutes with a 1 minute drying period or in a Joslyn resistometer using one of the cycles shown in tables 8 and 10. Optical densities were measured using an X-Rite 530P spectrodensitometer.

TABLE 7

Examples 4A-4G

| Ingredient | 4A grams | 4B grams | 4C grams | 4D grams | 4E grams | 4F grams | 4G grams |
|---|---|---|---|---|---|---|---|
| Bismuth subsalicylate | 2.36 | 2.36 | 2.36 | 2.36 | 2.36 | 2.36 | 2.36 |
| Sulfur | 7.22 | 7.22 | 7.22 | 7.22 | 7.22 | 7.22 | 7.22 |
| Lithium carbonate | 9.58 | 9.58 | 4.79 | 9.58 | 9.58 | 9.58 | 9.58 |
| Sodium carbonate | 0 | 1.2 | 1.2 | 0 | 0 | 0 | 0 |
| potassium carbonate | 0 | 0 | 0 | 1.2 | 0 | 0 | 0 |
| zinc carbonate | 0 | 0 | 0 | 0 | 1.2 | 0 | 0 |
| calcium carbonate | 0 | 0 | 0 | 0 | 0 | 1.2 | 0 |
| sodium bicarbonate | 0 | 0 | 0 | 0 | 0 | 0 | 0.8 |
| Binder solution | 60.84 | 59.64 | 64.43 | 59.64 | 59.64 | 59.64 | 60.04 |
| Total | 80 | 80 | 80 | 80 | 80 | 80 | 80 |

TABLE 8

Optical Density Results for Examples 4A-4G

| steam exposure | 4A | 4B | 4C | 4D | 4E | 4F | 4G |
|---|---|---|---|---|---|---|---|
| AMSCO 132° C., 4 min | 0.99 | 1.08 | 1.02 | 1.07 | 0.97 | 1.01 | 1.01 |
| color after AMSCO | brown | black | black | black | brown | brown | black |
| Resistometer 134° C., 2 min | 0.60 | 0.96 | 0.87 | 0.98 | 0.62 | 0.67 | 0.86 |
| Resistometer 134° C., 30 sec | 0.24 | 0.55 | 0.55 | 0.77 | 0.25 | 0.26 | 0.36 |
| Resistometer 121° C., 10 min | 0.82 | 1.00 | 0.94 | 1.00 | 0.87 | 0.86 | 0.90 |
| Resistometer 121° C., 3 min | 0.34 | 0.79 | 0.75 | 0.84 | 0.36 | 0.34 | 0.64 |
| OD difference between 134° C., 2 min and 121° C., 3 min cycles | 0.26 | 0.17 | 0.12 | 0.14 | 0.26 | 0.33 | 0.22 |

TABLE 9

Examples 4H-4N

| Ingredient | 4H grams | 4I grams | 4J grams | 4K grams | 4L grams | 4M grams | 4N grams |
|---|---|---|---|---|---|---|---|
| Bismuth subsalicylate | 2.36 | 2.36 | 2.36 | 2.36 | 2.36 | 2.36 | 2.36 |
| Sulfur | 7.22 | 7.22 | 7.22 | 7.22 | 7.22 | 7.22 | 7.22 |
| Lithium carbonate | 9.58 | 9.58 | 9.58 | 9.58 | 9.58 | 9.58 | 9.58 |
| sodium bicarbonate | 1.2 | 1.6 | 0 | 0 | 0 | 0 | 0 |
| potassium bicarbonate | 0 | 0 | 0.8 | 1.2 | 1.6 | 1.2 | 0 |
| sodium phosphate tribasic | 0 | 0 | 0 | 0 | 0 | 0 | 1.2 |
| Binder solution | 59.64 | 59.24 | 60.04 | 59.64 | 59.24 | 59.64 | 59.64 |
| Total | 80 | 80 | 80 | 80 | 80 | 80 | 80 |

TABLE 10

Optical Density Results for Examples 4H-4N

| steam exposure | 4H | 4I | 4J | 4K | 4L | 4M | 4N |
|---|---|---|---|---|---|---|---|
| AMSCO 132° C., 4 min | 1.11 | 1.10 | 0.96 | 1.02 | 1.07 | 1.00 | 1.00 |
| color after AMSCO | black | black | black | black | black | black | black |
| Resistometer 134° C., 2 min | 0.85 | 0.89 | 0.84 | 0.89 | 1.05 | 0.96 | 0.89 |
| Resistometer 134° C., 30 sec | 0.37 | 0.39 | 0.42 | 0.52 | 0.58 | 0.62 | 0.49 |

TABLE 10-continued

Optical Density Results for Examples 4H-4N

| steam exposure | 4H | 4I | 4J | 4K | 4L | 4M | 4N |
|---|---|---|---|---|---|---|---|
| Resistometer 121° C., 10 min | 1.01 | 1.02 | 0.91 | 0.93 | 1.06 | 0.96 | 0.94 |
| Resistometer 121° C., 3 min | 0.64 | 0.66 | 0.65 | 0.73 | 0.88 | 0.81 | 0.73 |
| OD difference between 134° C., 2 min and 121° C., 3 min cycles | 0.21 | 0.23 | 0.19 | 0.16 | 0.17 | 0.16 | 0.17 |

The results shown in Tables 8 and 10 show that the addition of a compound with relatively high water solubility that makes the indicator ink compositions alkaline on exposure to water vapor at elevated temperature, and/or reducing agents, increases the optical density of the autoclave tape backings after exposure to steam.

Examples 4A, 4E, and 4F (as comparative examples) do not contain such a compound (that is relatively highly water soluble and that makes the indicator ink compositions alkaline on exposure to water vapor at elevated temperature) and are brown after exposure to steam in an AMSCO sterilizer at 132° C. for 4 minutes. (The solubility of lithium carbonate in water at 20° C. is 1.3 g/100 ml). Zinc carbonate and calcium carbonate are essentially insoluble in water at 20° C.).

Examples 4B and 4C both contain sodium carbonate (solubility in water is 21.6 g/100 ml at 20° C.). Example 4D contains potassium carbonate (solubility in water is 112 g/100 ml at 20° C.). Examples 4G, 4H, and 4I contain sodium bicarbonate (solubility in water is 10 g/100 ml at 20 C). Examples 4J, 4K, 4L, and 4M contain potassium bicarbonate (solubility in water is 22.5 g/100 ml at 20° C.). Example 4N contains sodium phosphate tribasic (solubility in water is 16 g/100 ml at 20° C.

The resistometer measurements show high optical densities for the 134° C., 2 minute and 121° C., 10 minute cycles (the so-called ISO 11140 "pass" cycles) and lower optical densities for the 134° C., 30 second and 121° C., 3 minute cycles (the so-called ISO 11140 "fail" cycles). Furthermore, there is good discrimination between optical densities between the 134° C. 2 min cycle and the 121° C., 3 minute cycles, especially for examples 4G, 4H, 4I, and 4J.

All references and publications or portions thereof cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the embodiments provided below and equivalents thereof.

What is claimed is:

1. A chemical indicator composition comprising:
   a) a bismuth (III) compound comprising at least one organic group which includes 2 to 20 carbon atoms;
   b) elemental sulfur; and
   c) a reducing agent selected from the group consisting of ascorbic acid and its derivatives, tocopherols, gallates, t-butyl hydroquinones, napthylamines, polyphenols, and combinations thereof; and
   d) a compound which makes the composition alkaline when exposed to water vapor at an elevated temperature.

2. The composition of claim 1, wherein the reducing agent is present in at least 1 wt. % based on the total weight of the composition and at no more than 5 wt. % based on the total weight of the composition.

3. The composition of claim 1, wherein the compound which makes the composition alkaline has a solubility in water at 20° C. of more than 5 gram per 100 cubic centimeters of water.

4. The composition of claim 1, wherein the compound which makes the composition alkaline when exposed to water vapor at an elevated temperature is present at no more than 4 wt % based on the total weight of the composition.

5. The composition of claim 1, wherein the bismuth compound and the elemental sulfur are present in a weight ratio of not more than 2:3 and not less than 0.5:3; and wherein the elemental sulfur and the compound which makes the composition alkaline are present in a weight ratio of not more than 1:1 and not less than 1:5.

6. The composition of claim 1, further comprising a dye which causes the color of the composition in the presence of steam to become black; wherein without the dye, the color of the composition in the presence of steam would be brown.

7. The composition of claim 1, wherein the bismuth compound is bismuth subsalicylate.

8. The composition of claim 1, wherein the compound which makes the composition alkaline is selected from the group consisting of sodium carbonate, sodium bicarbonate, potassium carbonate, potassium bicarbonate, and sodium phosphate, or a combination thereof.

9. A chemical indicator composition comprising:
   a) a bismuth (III) compound comprising at least one organic group which includes 2 to 20 carbon atoms;
   b) elemental sulfur; and
   c) a compound which makes the composition alkaline when exposed to water vapor at an elevated temperature and is selected from the group consisting of potassium carbonate, potassium bicarbonate, and sodium phosphate.

10. A method of determining the effectiveness of a steam sterilization process, the method comprising:
    providing a chemical indicator comprising the chemical indicator composition of claim 1;
    placing the chemical indicator in a steam sterilization chamber;
    exposing the chemical indicator to steam at a temperature of at least 121° C.; and
    determining an optical density of the chemical indicator.

11. A chemical indicator comprising a substrate and the chemical indicator composition of claim 1 coated on at least a portion of a major surface of the substrate.

12. The chemical indicator of claim 11, wherein the substrate is coated with or impregnated with a saturant.

13. The chemical indicator of claim 11, further comprising a saturant layer covering the chemical indicator composition.

14. The chemical indicator of claim 13, further comprising a barrier layer covering the saturant layer and the substrate.

15. The chemical indicator of claim 11, further comprising an adhesive layer covering at least a portion of a second major surface of the substrate opposite chemical indicator composition.

16. The composition of claim 1, wherein the reducing agent facilitates formation of sulfide groups that react with the bismuth (III) compound to darken the color of the indicator composition upon exposure to steam.

17. The composition of claim 1, wherein the reducing agent is selected from the group consisting of tocopherols, napthylamines, polyphenols, and combinations thereof.

18. The composition of claim 1, wherein the reducing agent is selected from ascorbic acid and its derivatives, and combinations thereof.

19. A chemical indicator composition comprising:
    a) a bismuth (III) compound comprising at least one organic group which includes 2 to 20 carbon atoms;
    b) elemental sulfur;
    c) a compound that makes the composition alkaline when exposed to water vapor at an elevated temperature; wherein the compound has a solubility in water at 20° C. of more than 5 grams/100 ml; and
    d) a reducing agent selected from the group consisting of tocopherols, napthylamines, polyphenols and combinations thereof.

* * * * *